(12) United States Patent
Yokozeki et al.

(10) Patent No.: US 7,754,466 B2
(45) Date of Patent: Jul. 13, 2010

(54) METHOD FOR PRODUCING DIPEPTIDES

(75) Inventors: Kenzo Yokozeki, Kanagawa (JP); Sonoko Suzuki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 1685 days.

(21) Appl. No.: 10/476,885

(22) PCT Filed: Jul. 26, 2002

(86) PCT No.: PCT/JP02/07634

§ 371 (c)(1), (2), (4) Date: Nov. 14, 2003

(87) PCT Pub. No.: WO03/010189

PCT Pub. Date: Feb. 6, 2003

(65) Prior Publication Data

US 2004/0137558 A1 Jul. 15, 2004

(30) Foreign Application Priority Data

Jul. 26, 2001 (JP) .............................. 2001-226568
Oct. 5, 2001 (JP) .............................. 2001-310547

(51) Int. Cl.
*C12N 1/20* (2006.01)
*C12P 21/06* (2006.01)
*G01N 33/58* (2006.01)

(52) U.S. Cl. ..................... 435/252.3; 435/68.1; 435/7.1
(58) Field of Classification Search .............. 435/252.3, 435/7.1; 564/135
See application file for complete search history.

(56) References Cited

U.S. PATENT DOCUMENTS 5,518,905 A 5/1996 Kotani et al.

FOREIGN PATENT DOCUMENTS

| EP | 0 278 787 | 8/1988 |
|---|---|---|
| EP | 311057 | 4/1989 |
| EP | 636695 | 2/1995 |
| GB | 2250023 | 5/1997 |
| JP | 53-092729 | 8/1978 |
| JP | 1-96194 | 4/1989 |
| JP | 3-87195 | 4/1991 |
| JP | 6-217785 | 8/1994 |
| JP | 6-234715 | 8/1994 |
| JP | 7-39385 | 2/1995 |
| JP | 9-47294 | 2/1997 |
| JP | 9-248197 | 9/1997 |
| JP | 10-174597 | 6/1998 |
| JP | 2000-78971 | 3/2000 |
| WO | 90/01555 | 2/1990 |
| WO | 98/16546 | 4/1998 |

OTHER PUBLICATIONS

Durham, D.R. , Applied and Environmental Microbiology vol. 56, No. 8, pp. 2277-2281, Aug. 1990.*
Furst, P. , Nutrition, vol. 13 Nos. 7/8 , pp. 731-737, 1997.*
U.S. Appl. No. 10/855,533, filed May 28, 2004, Hara, et al.
U.S. Appl. No. 11/330,076, filed Jan. 12, 2006, Yokozeki, et al.
Ryunosuke Muneyuki: "Koso o mochiiru peptide gosei—atarashii suiyosel estei kishitsu no gosei to koso no koteika -" Journal of the Chemical Society of Japan, No. 9, pp. 1336-1344 1983 (with English translation).
Sawao Murao et al.: "Isolation of propioxatin A from *Actinosynnema* sp. SI-23 during a screening for serratiapiscatorum metalloproteinase Inhibitors" Biosci. Biotech. Biochem., vol. 61, No. 3, pp. 561-562, 1997.
Tetsuo Muro et al.: "Purification and some properties of a protease from *Streptomyces limosus*" Biosci. Biotech. Biochem., vol. 59, No. 3, pp. 474-478, 1995.
Bull. Chem. Soc. Jpn., vol. 34, p. 739 May 1961.
Bull. Chem. Soc. Jpn., vol. 35, pp. 1966-1970 1962.
Biochemical J., vol. 163, pp. 531-542 1977.
Bull. Chem. Soc. Jpn., vol. 37, pp. 200-203 1963.
T. Liesen et al, "ERA, a novel cis-acting element required for autoregulation and ethanol repression of PDC1 transcription in *Saccharomyces cerevisiae*.", *Mol. Microbiol.*, 1996, vol. 21, pp. 621-632.
S. Hohmann, "PDC6, a weakly expressed pyruvate decarboxylase gene from yeast, is activated when fused spontaneously under the control of the PDC1 promoter.", *Curr. Genet.*, 1991, vol. 20, pp. 373-378.

* cited by examiner

*Primary Examiner*—Robert Mondesi
*Assistant Examiner*—Khatol Shahnan-Shah
(74) *Attorney, Agent, or Firm*—Oblon, Spivak, McClelland, Maier & Neustadt, L.L.P.

(57) ABSTRACT

The present invention provides a method of producing a dipeptide from starting materials that are available at low costs through a route industrially advantageous and simple. Dipeptides are produced from amino acid esters and amino acids by using a culture of a microbe having an ability to produce a dipeptide from an amino acid ester and an amino acid, microbial cells separated from the culture, or treated microbial cell product.

7 Claims, No Drawings

METHOD FOR PRODUCING DIPEPTIDES

TECHNICAL FIELD

The present invention relates to a simple and cheaper method for producing dipeptides.

BACKGROUND ART

Dipeptides find uses in various fields. For example, the dipeptides are used as raw materials for pharmaceuticals and functional foods. For example, L-alanyl-L-glutamine is used as a component of serum-free media, because, it is more stable and more soluble in water than L-glutamine.

The dipeptides are generally produced by chemical synthetic methods. Concretely, following methods are known. Use N-benzyloxycarbonylalanine (hereinafter, referred to as "Z-alanine") and protected L-glutamine (Bull. Chem. Soc. Jpn., 34, 739 (1961) and Bull. Chem. Soc. Jpn., 35, 1966 (1962)), use -Z-alanine and protected L-glutamic acid-γ-methyl ester (Bull. Chem. Soc. Jpn., 37, 200 (1964)), use Z-alanine ester and non-protected glutamine (JP-1-96194A), and synthesize N-(2-substituted)-propionylglutamine derivative as an intermediate using a 2-substituted propionyl halide as a raw material (JP-6-234715A).

However, all of these methods require introduction and elimination of protective groups or synthesis of intermediates, so that none of them is industrially advantageous and fully satisfactory.

As representative production methods for dipeptides using enzymes, there have been known a condensation reaction using an N-protected-C-nonprotected carboxyl component and an N-nonprotected-C-protected amine component (hereinafter, "reaction 1") and a substitution reaction using an N-protected-C-protected carboxyl component and an N-nonprotected-C-protected amine component (hereinafter, "reaction 2"). An example of the reaction 1 is a method for producing a Z-aspartylphenylanaline methyl ester from Z-aspartic acid and phenylalanine methyl ester (JP-53-92729A). An example of the reaction 2 is a method for producing acetylphenylalanylleucinamide from acetylphenylalanine ethyl ester and leucinamide (Biochemical J., 163, 531 (1977)). There are very few reports of use of an N-nonprotected-C-protected carboxyl component. An example of a substitution reaction using an N-nonprotected-C-protected carboxyl component and an N-nontroteced-C-protected amine component (hereinafter, "reaction 3") includes, for example, a method for producing arginylleucinamide from arginine ethyl ester and leucinamide as described in WO90/01555. An example of a substitution reaction using an N-nonprotected-C-protected carboxyl component and an N-nonprotected-C-nonprotected amine component (hereinafter, "reaction 4") includes, for example, a method for producing tyrosylalanine from tyrosine ethyl ester and alanine as described in EP-278787A. Production methods that can be most inexpensive among these production methods are those using reactions that fall within the category of the reaction 4 in which the number of the protective groups in the components used is the smallest.

However, enzymes used in the conventional example of the reaction 4 (EP-278787A) include reagents of relatively expensive carboxypeptidase preparations derived from yeast that belongs to the genus Saccharomyces or fungi or plants. The produced dipeptides contain amino acids with relative high degrees of hydrophobicity. EP-278787A discloses no method that uses an enzyme derived from yeast other than that belongs to the genus Saccharomyces. Further, no method has been known that produces alanylglutamine or alanylasparagine with a high hydrophilicity. Thus, development of a production method for such peptides on an industrial scale and at a reduced cost has been demanded.

DISCLOSURE OF THE INVENTION

It is an object of the present invention to provide a method for producing a dipeptide using a starting material that is available at a reduced cost and an enzyme source that is supplied at a reduced cost (cultures of microbes, microbial cells, treated microbial cell products) through a route that is industrially advantageous and simple.

As a result of extensive studies, the inventors of the present invention have found that microbes that belong to certain bacteria and yeasts and can be cultured at low costs have abilities of producing dipeptides from L-amino acid esters and L-amino acids that are available at low costs, thus accomplishing the present invention.

The present invention provides:

[1] A method for producing a dipeptide from an amino acid ester and an amino acid using one selected from the group consisting of a culture of a microbe, microbial cells separated from the culture, a treated microbial cell product, and a peptide-forming enzyme derived from the microbe, wherein the microbe belongs to a genus selected from the group consisting of Achromobacter, Acinetobactor, Aeromonas, Agrobacterium, Alcaligenes, Arthrobacter, Beijerinckia, Brevibacterium, Clavibacter, Cryseobacterium, Escherichia, Enterobacter, Erwinia, Flavobacterium, Kluyvera, Microbacterium, Micrococcus, Mycoplana, Pantoea, Propionibacterium, Listonella, Rhizobium, Rhodococcus, Salmonella, Sarcina, Serratia, Stenotrophomonas, Staphylococcus, Streptomyces, Vibrio, Xanthomonas, Bullera, Candida, Cryptococcus, Filobacidium, Geotrichum, Pachysolen, Rhodosporidium, Rhodotorula, Saccharomyces, Sporoboromyces, Tremella, Torulaspora, Torulopsis, Acetobacter, Gluconobacter, Gluconacetobacter, Asaia, Zucharibacter, Actinomadura, Kitasatosporia, Micromonospora, Nocardia, Oerskovia, Saccharothrix, and Streptoverticillium and has an ability of producing the dipeptide from the amino acid ester and the amino acid.

[2] The method for producing a dipeptide according to [1] described above, further including adding a metal enzyme inhibitor to a reaction mixture in producing the dipeptide from the amino acid ester and the amino acid using one selected from the group consisting of the culture of the microbe, the cell of the microbe separated from the culture, the treated microbial cell product, and the peptide-forming enzyme derived from the microbe.

[3] The method for producing a dipeptide according to [1] or [2] described above, wherein the amino acid ester is an L-alanine ester.

[4] The method for producing a dipeptide according to any one of [1] to [3] described above, wherein the amino acid is L-glutamine.

BEST MODE FOR CARRYING OUT THE INVENTION

The method for producing a dipeptide according to the present invention uses one selected from the group consisting of a culture of a microbe, microbial cells separated from the culture, a treated microbial cell product, and a peptide-forming enzyme derived from the microbe, wherein the microbe has an ability to produce the dipeptide from an amino acid ester and an amino acid. Reaction involved in the method for producing a dipeptide according to the present invention is represented by the following reaction scheme. As illustrated in the following reaction scheme, "dipeptide" as used herein refers to a peptide polymer that has one peptide bond.

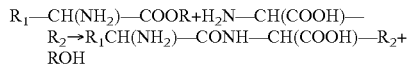

$R_1$—CH(NH$_2$)—COOR+H$_2$N—CH(COOH)—$R_2$→$R_1$CH(NH$_2$)—CONH—CH(COOH)—$R_2$+ ROH (where R represents a substituted or unsubstituted hydrocarbon chain; $R_1$ represents a side chain of an amino acid ester; and $R_2$ represents a side chain of an amino acid.).

The amino acid ester is available at a low cost. The method of the present invention in which an amino acid ester and a nonprotected amino acid as starting materials are reacted in an aqueous solution using a bacterium or a yeast as an enzyme source is a novel method for producing a dipeptide is an entirely new approach. This method makes it possible to provide a dipeptide that is useful as a material for pharmaceuticals and functional foods at a low cost.

Hereinafter, explanation will be given in the following order:

[I] Microbes having an ability to produce a dipeptide from an amino acid ester and an amino acid,
[II] Method for producing a dipeptide, and
[III] Isolation and so forth of a DNA encoding a protein having peptide-forming activity.

[I] Microbes Having Ability of Producing a Dipeptide from an Amino Acid Ester and an Amino Acid The microbes that can be used in the present invention are not particularly limited and any microbe that has an ability to produce a dipeptide from an amino acid ester and an amino acid can be used. The microbes that have an ability of producing a dipeptide from an amino acid ester and an amino acid include those microbes that belong to the genera *Achromobacter, Acinetobactor, Aeromonas, Agrobacterium, Alcaligenes, Arthrobacter, Beijerinckia, Brevibacterium, Clavibacter, Cryseobacterium, Escherichia, Enterobacter, Erwinia, Flavobacterium, Kluyvera Microbacterium, Micrococcus, Mycoplana, Pantoea, Propionibacterium, Listonella, Rhizobium, Rhodococcus, Salmonella, Sarcina, Serratia, Stenotrophomonas, Staphylococcus, Streptomyces, Vibrio, Xanthomonas, Bullera, Candida, Cryptococcus, Filobacidium, Geotrichum, Pachysolen, Rhodosporidium, Rhodotorula, Saccharomyces, Sporoboromyces, Tremella, Torulaspora, Torulopsis, Acetobacter, Gluconobacter, Gluconacetobacter, Asaia, Zucharibacter, Actinomadura, Kitasatosporia, Micromonospora, Nocardia, Oerskovia, Saccharothrix,* or *Streptoverticillium.* Specifically, the following microbes are exemplified.

*Achromobacter delmarvae* FERM BP-6988
*Acinetobactor johnsonii* ATCC 9036
*Aeromonas salmonicida* ATCC 14174
*Agrobacterium tumefaciens* IFO 3058
*Alcaligenes faecalis* ATCC 8750
*Arthrobacter citreus* ATCC 11624
*Beijerinckia indica* ATCC 9037
*Brevibacterium roseum* ATCC 13825
*Clavibacter michiganense* ATCC 7429
*Cryseobacterium meningosepticum* ATCC 13253
*Escherichia coli* ATCC 13071
*Enterobacter aerogenes* ATCC 13048
*Erwinia amylovora* IFO 12687
*Flavobacterium resinovorum* ATCC 12524
*Kluyvera citrophila* FERM BP-6564
*Microbacterium imperiale* ATCC 8365
*Micrococcus luteus* ATCC 11880
*Mycoplana bullata* ATCC 4278
*Pantoea ananatis* ATCC 23822
*Propionibacterium shermanii* FERM BP-8100
*Listonella anguillarum* ATCC 19264
*Rhizobium radiobacter* ATCC 4720
*Rhodococcus rhodochrous* ATCC 21198
*Salmonella typhimurium* FERM BP-6566
*Sarcina lutea* FERM BP-6562
*Serratia grimesii* ATCC 14460
*Staphylococcus aureus* ATCC 12600
*Stenotrophomonas maltophilia* ATCC 13270
*Streptomyces lavendulae* ATCC 11924
*Vibrio tyrogenes* FERM BP-5848
*Xanthomonas maltophilia* FERM BP-5568
*Bullera alba* FERM BP-8099
*Candida krusei* IFO 0011
*Cryptococcus terreus* IFO 0727
*Filobacidium capsuligenum* IFO 1119
*Geotrichum amycelium* ATCC 56046
*Pachysolen tannophilus* IFO 1007
*Rhodosporidium dibovatum* IFO 1829
*Rhodotorula minuta* IFO 0879
*Saccharomyces unisporus* IFO 0724
*Sporoboromyces salmonicolor* IFO 1038
*Tremella foliacea* IFO 9297
*Torulaspora delbrueckii* IFO 1083
*Torulopsis ingeniosa* FERM BP-8098
*Gluconacetobacter liquefaciens* IFO 12388
*Acetobacter orleanensis* IFO 3223
*Acetobacter pasteurianus* ATCC 9325
*Gluconobacter oxydans* ATCC 621
*Gluconobacter oxydans* IFO 3171
*Gluconacetobacter hansenii* JCM 7643
*Asaia ethanolifaciens* FERM BP-6751
*Zucharibacter floricola* FERM BP-6752
*Actinomadura madurae* ATCC 19425
*Kitasatosporia griseola* IFO 14371
*Micromonospora chersina* ATCC 53710
*Nocardia globerula* ATCC 21602
*Oerskovia turbata* FERM BP-8122
*Saccharothrix australiensis* IFO 14444
*Streptoverticillium mobaraensis* IFO-13819

Among these strains, those strains whose ATCC numbers are recited have been deposited at American Type Culture Collection (P.O. Box 1549, Manassas Va. 20110, U.S.A.) and are furnished by referring to the respective numbers. Among those strains whose IFO numbers are recited have been deposited at Institute for Fermentation, Osaka, Foundation (17-85, Juso-honmachi 2-chome, Yodogawa-ku, Osaka 532-8686, Japan) and are furnished by referring to the respective numbers. Among those strains whose JCM numbers are recited have been deposited at The Institute of Physical and Chemical Research (2-1, Hirosawa, Wako-shi, Saitama-ken 351-0106, Japan) and are furnished by referring to the respective numbers. Among those strains whose FERM numbers are described are microbes that have been deposited at National Institute of Advanced Industrial Science and Technology at Chuo Dai-6, 1-1 Higashi 1-Chome, Tsukuba-shi, Ibaraki-ken, 305-8566, Japan) and given receipt numbers. Original b deposition of *Achromobacter delmarvae* FERM BP-6988 made on Jan. 16, 1998 has been transferred to international deposition on Jan. 6, 2000. Original deposition of *Kluyvera citrophila* FERM BP-6564 made on Apr. 23, 1985 has been transferred to international deposition on Nov. 2, 1998. Original deposition of *Propionibacterium shermanii* FERM BP-8100 made on Dec. 4, 1987 has been transferred to international deposition on Jul. 1, 2002. Original deposition of *Salmonella typhilium* FERM BP-6566 made on Jul. 11, 1987 has been transferred to international deposition on Nov. 2, 1998. Original deposition of *Sarcina lutea* FERM BP-6562 made on Jan. 20, 1984 has been transferred to international deposition on Nov. 2, 1998. Original deposition of *Vibrio tyrogenes* FERM BP-5848 made on Apr. 25, 1983 has been transferred to international deposition on Mar. 4, 1997. Original deposition of *Xanthomonas maltophilia* FERM BP-5568 made on Jun. 14, 1995 has been transferred to international deposition on Jun. 14, 1996. Original deposition of *Bullera alba* FERM BP-8099 made on Dec. 24, 1984 has been transferred to international deposition on Jul. 1, 2002. Original deposition of *Torulopsis ingeniosa* FERM BP-8098 made on Aug. 24, 1970 has been transferred to international deposition on Jul. 5, 2002. Original depositions of *Asaia ethanolifaciens* FERM BP-6751 (indication of microbe; Bacterium 528 AJ14757) and *Zucharibacter floricola* FERM BP-6752 (indication of microbe; Bacterium S877 AJ14758) made on Jun. 18, 1998 have been transferred to international depositions on Jun. 14, 1999. *Oerskovia turbata* FERM BP-8122 has been internationally deposition on Jul. 22, 2002.

Either wild strains or mutant strains may be used as these microbes. Even recombinant strains that are induced by genetic techniques such as cell fusion or genetic engineering and so forth may be used as these microbes.

Cells of such a microbe can be obtained by culturing and proliferating the microbe in a proper medium. The medium may be any medium that allows the microbe to proliferate. For example, the medium may be an ordinary medium that contains a carbon source, a nitrogen source, a phosphorus source, a sulfur source, and inorganic ions and further an organic nutrient source, if necessary, that are commonly used.

For example, as the carbon source, any carbon source can be used so far as the above-mentioned microbe can utilize it. Specifically, sugars such as glucose, fructose, maltose, and amylose; alcohols such as sorbitol, ethanol, and glycerol; organic acids such as fumaric acid, citric acid, acetic acid, and propionic acid as well as salts thereof; hydrocarbons such as paraffin; or mixtures thereof may be used.

As the nitrogen source, ammonium salts of inorganic acids, such as ammonium sulfate and ammonium chloride; ammonium salts of organic acids, such as ammonium fumarate and ammonium citrate; nitrates such as sodium nitrate and potassium nitrate; organic nitrogen compounds such as peptone, yeast extracts, meat extracts and corn steep liquor; or mixtures of these may be used.

In addition, inorganic salts, trace metal salts, vitamins and the like nutrient sources that are used in ordinary media may be used as appropriate mixtures.

Culturing conditions are not particularly limited. For example, culture may be performed under aerobic conditions with properly controlling pH and temperature within the ranges of a pH of from 5 to 8 and a temperature of from 15° C. to 40° C. for from about 12 hours to about 48 hours.

[II] Production Method for Dipeptides

The method for producing a dipeptide according to the present invention includes producing a dipeptide from an amino acid ester and an amino acid using a culture of a microbe that has an ability to produce the dipeptide from amino acid ester and the amino acid, microbial cells separated from the culture, treated microbial cell product or a peptide-forming enzyme derived from the microbe.

The peptide-forming enzyme produced by the microbe has activity to produce a dipeptide from an amino acid ester and an amino acid.

Method of acting peptide-forming enzyme produced by the microbe on the amino acid ester or amino acid may be a method in which substrates are directly added to the medium while the above-mentioned microbe is being cultured. Alternatively, a method may be used in which cells are separated by centrifugation from the medium after completion of the culture or microbe culture and the cells as they are or after they are washed are resuspended in a buffer and the amino acid ester and amino acid are added to the resultant. Alternatively, cells immobilized by a known method such as a polyacrylamide gel method, a carrageenan method or an alginate gel method may be used.

Further, as the treated microbial cell product may be used cell fragments, acetone-treated microbial cells, or freeze-dried microbial cells. For crushing microbial cells, ultrasonic crushing, French press crushing, glass bead crushing or the like method may be used. Further, in the case where lysis is performed, a method of using egg white lysozyme, a method of using peptidase treatment or suitable combinations of these may be used.

Further, a peptide-forming enzyme may be recovered from the treated microbial cell product and the peptide-forming enzyme may be used as a crude enzyme solution or the enzyme may be purified before use as necessary. As the method for purifying the enzyme from the culture, an ordinary enzyme purification method may be used. Specifically, the above-mentioned peptide-forming enzyme is purified through the following steps; collecting cells by use of centrifugation or the like, crushing the cells by use of a mechanical method such as ultrasonic treatment, glass beads, or a dyno mill, removing solid matter such as cell debris by use of centrifugation to obtain a crude enzyme, and then performing ultracentrifugal fractionation, salting out, organic solvent precipitation, ion exchange chromatography, adsorption chromatography, gel filtration, hydrophobicity chromatography or the like.

Note that "peptide-forming enzyme derived from a microbe" includes not only an enzyme obtained by the above-mentioned purification step from the treated microbial cell product but also enzymes produced by expressing gene of the enzyme in a heterogeneous or homogeneous strain host, i.e., produced by a so-called a genetic engineering technique.

That is, an enzyme and all those substances that contain the enzyme can be used so far as they are fractions that have activity to produce a dipeptide from an amino acid ester and an amino acid. The "enzyme-containing substances" as used herein may be any substance that contains the enzyme and include as specific forms a culture of a microbe that produces the enzyme, microbial cells separated from the culture, a treated microbial cell product and so forth. The culture of a microbe is a matter that is obtained by culturing a microbe and specifically means a mixture of microbial cells, a medium used for culturing the microbe, and a substance produced by the cultured microbe. Further, the microbial cells may be washed and used as washed microbial cells. Furthermore, the treated cell product includes crushed microbial cells, lysed microbial cells, freeze-dried microbial cells and so forth and further crude enzymes recovered by treating the microbial cells and purified enzyme obtained by further purifying the crude enzyme. As the purified enzyme may be used purified enzymes obtained by various purification methods. Also, there may be used immobilized enzymes obtained by immobilizing the partially purified enzymes by a covalent bond method, an adsorption method, an inclusion method or the like. Further, some microbes are partly lysed during culture. In such as case, culture supernatant may be utilized as a substance that contains the enzyme.

Note that in the case where the culture, cultured microbial cells, washed microbial cells, treated microbial cells obtained by crushing or lyzing microbial cells are used, often enzymes exist that do not participate in production of peptides but decompose the produced peptide. In this case, it is sometimes preferable that a metal enzyme inhibitor, for example, a metal protease inhibitor such as ethylenediaminetetraacetic acid (EDTA) is added. Addition amount is in the range of from 0.1 millimolar (mM) to 100 mM, preferably from 1 mM to 50 mM.

For the amount of the enzyme or enzyme containing-substance to be used, amounts in which a target effect is exhibited (hereinafter, "effective amount") are enough. The effective amount can be readily obtained by a person having ordinary skill in the art by conducting a simple preliminary experiment. For example, in the case where washed microbial cells are used, the effective amount is 1 gram (hereinafter, "g") to 500 g per liter of the reaction mixture.

As the amino acid ester, any amino acid ester may be used as far as it can give rise to a dipeptide together with an L-amino acid in accordance with the substrate specificity of the peptide-forming enzyme. Examples of such include methyl esters, ethyl esters, n-propyl esters, isopropyl esters, n-butyl esters, isobutyl esters, tert-butyl esters, etc. of L-amino acids. Not only L-amino acid esters that correspond to natural type amino acids but also L-amino acid esters or D-amino acid esters that correspond to nonnatural type amino acids or derivatives thereof may also be used. In the present invention, preferably L-alanine esters may be used as the amino acid esters. The amino acid is not particularly limited and any known amino acid may be used so far as it can form a dipeptide together with an amino acid ester in accordance with the substrate specificity of the peptide-forming enzyme. For example, the amino acids include L-amino acids, C-protected L-amino acids, D-amino acids, C-protected D-amino acids, amines and so forth. Further, as the amines, not only natural type amines but also nonnatural type amines or derivatives thereof are exemplified. Furthermore, as the amino acids, not only natural type amino acids but also nonnatural type amino acids or derivatives thereof may be exemplified. In addition to α-amino acids, β-, γ-, ω-, etc. amino acids may also be exemplified. In the present invention, preferably L-glutamine is used as the amino acid.

Concentrations of the amino acid ester and of amino acid, starting materials, are each from 1 mM to 10 M, preferably from 0.05 M to 2 M. In some cases, it is preferable that the amino acid is added in an amount equimolar or excess molar with respect to the amino acid ester. Further, if necessary, for example, if the substrates in high concentrations inhibit the reaction, the substrates may be added in sequence after diluted to concentrations that do not inhibit the reaction.

Reaction temperature is from 3° C. to 70° C., preferably from 5° C. to 50° C. Reaction pH is from 2 to 12, preferably 3 to 11. Thus, by performing the reaction for from 2 hours to 48 hours, a dipeptide is produced and accumulated in the reaction mixture. The produced dipeptide is recovered by a conventional method and, if necessary, purified.

[III] Isolation and so Forth of DNA Encoding a Protein that has Peptide-Forming Activity

[III-1] Isolation of DNA

The microbes used in the present invention have ability to synthesize dipeptides from amino acid esters and amino acids. It is also possible to obtain proteins that produce dipeptides from amino acid esters and amino acids (peptide-forming enzyme) by isolating DNAs encoding proteins that produce dipeptides from amino acid esters and amino acids from the above-mentioned microbes by using a genetic engineering technique and making transformants. Hereinafter, an embodiment of a method of isolating a DNA encoding a protein that produces a dipeptide from an L-amino acid ester and an L-amino acid from a microbe and making a transformant will be described.

First, a peptide forming enzyme is obtained from the above-mentioned microbe as described above in connection with [II] Production method for dipeptides. And then, amino acid sequence of the purified peptide-forming enzyme is determined by using the Edman method (Edman, P., Acta Chem., Scand., 4, 227 (1950)) or by using a sequencer manufactured by Applied Biosystems, Inc. Amino acid sequence of 30 residues from the N-terminal of the purified peptide-forming enzyme is determined and based on the elucidated amino acid sequence can be deduced a base sequence of a DNA that encodes the peptide-forming enzyme. To deduce the base sequence of a DNA, there are adopted universal codons.

Based on the deduced base sequence, a DNA molecule with about 30 base pairs is synthesized. Method for synthesizing the DNA molecule is disclosed in Tetrahedron Letters, 22, 1859 (1981)). Also, the DNA molecule can be synthesized by using a synthesizer manufactured by Applied Biosystems, Inc. The DNA molecule can be utilized as a probe when a full-length DNA encoding a peptide-forming enzyme is isolated from the chromosome gene library of a microbe. Alternatively, the DNA molecule can be used as a primer when a DNA encoding a peptide-forming enzyme is amplified by a PCR method. However, the DNA that is amplified by using the PCR method does not contain a full-length DNA encoding the peptide-forming enzyme, so that the full-length DNA encoding the peptide-forming enzyme is isolated from the chromosome gene library of the microbe by using the DNA that is amplified by using the PCR method.

The PCR method is described in White, T J. et al., Trends Genet., 5, 185 (1989), etc. The method of preparing a chromosomal DNA and the method of isolating a target DNA molecule from a gene library are described in "Molecular Cloning", 2nd edition, Cold Spring Harbor Press (1989), etc.

The method of determining the base sequence of a DNA encoding the isolated peptide-forming enzyme is described in "A Practical Guide to Molecular Cloning", John Wiley & Sons, Inc. (1985). Further, the base sequence can be determined by using a sequencer manufactured by Applied Biosystems, Inc.

The DNA that can be used in the present invention is not limited to the DNAs obtained as described above. Even those DNAs that are obtained by applying artificial mutation to a DNA encoding a peptide-forming enzyme, which DNA is isolated from a chromosomal DNA of a cell of a specified microbe, are DNAs that can be used in the present invention, if such DNAs encode peptide-forming enzyme. A method that is frequently used as a method of artificially applying mutation is a site-directed mutagenesis as described in Method. in Enzymol., 154 (1987).

Further, the DNA that can be used in the present invention also includes a DNA having a base sequence that hybridizes with a polynucleotide (DNA or RNA) having a base sequence complementary to the base sequence of the DNA isolated from a chromosomal DNA as described above under a stringent condition and encoding a protein having a peptide-forming activity. The term "under a stringent condition" as used herein refers to a condition under which a so-called specific hybrid is formed but no non-specific hybrid is formed. It is difficult to precisely express this condition in numerical values. For example, mention may be made of a condition under which DNAs having a high homology, for example, 50% or more, preferably 80% or more, more preferably 90% or more, hybridize with each other and DNAs having a lower homology than these do not hybridize with each other, or ordinary conditions for rinse in Southern hybridization under which hybridization is performed at 60° C. in a salt concentration corresponding to 1×SSC and 0.1% SDS, preferably 60° C., 0.1×SSC, and 0.1% SDS, more preferably 65° C., 0.1×SSC, and 0.1% SDS. The activity of peptide-forming enzyme is as already explained above. However, in the case of the base sequence that hybridizes with a complementary base sequence under a stringent condition, it is desirable that the protein encoded thereby retain an enzyme activity of 10% or more, more preferably 50% or more of the enzyme activity of the protein having the original amino acid sequence be retained under conditions of 50° C. and pH 8.

Further, proteins that are substantially encoded by the isolated DNA can also be used in the present invention. Therefore, in the present invention, there can be used also a DNA encoding a protein that contains substitution, deletion, insertion, addition or inversion of one or a few amino acid residues in the amino acid sequence encoded by the isolated DNA and that has a peptide-forming activity that catalyzes reaction in which a dipeptide is produced from an L-amino acid and an L-amino acid. The term "a few" is used herein in connection with the number of amino acid residues in the range where the three-dimensional structure of protein or activity of peptide-forming enzyme is not significantly hindered or deteriorated. Concretely, "a few" means from 2 to 50, preferably 2 to 30, more preferably 2 to 10. The activity of peptide-forming enzyme is as already explained above. However, in the case of an amino acid sequence that contains substitution, deletion, insertion, addition or inversion of one or a few amino acids, it is desirable that the amino acid sequence retain an enzyme activity of 10% or more, more preferably 50% or more of that of the protein having the original amino acid sequence under conditions of 50° C. and pH 8.

As described above, when a DNA is isolated from a microbe, the following DNAs can be advantageously used in the present invention. Note that, for example, a specified base sequence of the isolated DNA is named base sequence y and an amino acid sequence encoded by the base sequence is named amino acid sequence Y. The DNAs that can be used in the present invention are:

(i) A DNA consisting of the base sequence y,
(ii) A DNA that hybridizes with a base sequence complementary to the base sequence y under a stringent condition and that encodes a protein having a dipeptide-forming activity that catalyzes a reaction in which a dipeptide is produced from an L-amino acid ester and an L-amino acid,
(iii) A DNA that encodes a protein having the amino acid sequence Y, and
(iv) A DNA that encodes a protein having an amino acid sequence corresponding to the amino acid sequence Y that contains substitution, deletion, insertion, addition or inversion of one or a few amino acids and having a peptide-forming activity that catalyzes a reaction in which a dipeptide is produced from an L-amino acid ester and an L-amino acid.

[III-2] Preparation of Transformants

Next, the construction of transformants that express a protein having a peptide-forming activity will be explained. A number of cases in which enzymes, physiologically active substances and the like useful proteins are produced utilizing a recombinant DNA technology have been known. Use of the recombinant DNA technology enables mass production of useful proteins existing in minute amounts in nature.

Preferable examples of the transformants that can be used in the method of the present invention include transformants that can express proteins such as those described in (A), (B) or (C) below:

(A) A protein that has the amino acid sequence Y,
(B) A protein that has an amino acid sequence corresponding to the amino acid sequence Y that contains substitution, deletion, insertion, addition or inversion of one or a few amino acids and has a peptide-forming activity that catalyzes a reaction in which a dipeptide is produced from an L-amino acid ester and an L-amino acid, and
(C) A protein encoded by a DNA that hybridizes with a polynucleotide consisting of a base sequence complementary to the base sequence y under a stringent condition and encodes a protein having a peptide-forming activity that catalyzes a reaction in which a dipeptide is produced from an L-amino acid ester and an L-amino acid.

To prepare transformants that express proteins (A) to (C) having a peptide-forming activity, it is only necessary that the DNAs (i), (ii), (iii) or (iv) mentioned above in connection with the explanation of [111-1] Isolation of DNA be introduced in host cells. That is, the DNA of (i), (ii), (iii) or (iv) is incorporated in an expression vector that can be expressed in the host cell and introduced in the host cell.

The mutation as mentioned above in (B) can be obtained by, for example, a site-directed mutagenesis by modifying the base sequence of the gene of the enzyme of the present invention so that the amino acid at a specified site of the gene of the enzyme can be substituted, deleted, inserted or added. The DNA modified as described above can also be obtained by a conventionally known mutation treatment. The mutation treatment includes, for example, a method in which a DNA that encodes the enzyme of the present invention is treated in vitro with hydroxylamine or the like, and a method in which a bacterium that belongs to the genus *Escherichia* possessing a DNA that encodes the enzyme of the present invention is treated with a mutagen conventionally used for artificial mutation, such as ultraviolet ray, N-methyl-N'-nitro-N-nitrosoguanidine (NTG), or nitrous acid.

When a protein is mass-produced by using the recombinant DNA technology, a preferable embodiment includes a mode in which the protein molecules associate to form inclusion body of protein in the transformant that produces the protein. This expression production method has an advantage, for example, in that the target protein is protected from digestion by proteases that exist in the microbial cells and that the target protein can be easily purified by crushing the microbial cells and subsequent centrifugation operation.

The inclusion body of protein thus obtained is solubilized with a protein modifier and converted into a physiologically active protein that is properly folded after passing through an activating reconstitution operation by removing the modifier. There are many examples including, for example, activating reconstitution of human interleukin-2 (JP-61-257931A).

To obtain an activated type protein from the inclusion body of protein, a series of operations such as solubilization and activating reconstitution are necessary, so that the operation becomes more complicated than the case in where the activated type protein is directly produced. However, in the case where a protein that influences on the growth of microbial cells is mass-produced in the cells, the influence can be suppressed by allowing the protein to be accumulated in the cells in the form of an inactive inclusion body of protein.

The method in which a target protein is mass-produced as an inclusion body includes a method in which the target protein is allowed to be expressed alone under control of a potent promoter, and a method in which the target protein is allowed to be expressed as a fused protein with a protein whose mass expression has been known.

Further, it is effective to arrange a recognition sequence for recognizing a restriction protease at a proper site in order to cut out the target protein after it is allowed to be expressed as a fused protein.

When a protein is mass-produced by using the recombinant DNA technology, the host cells to be transformed may be bacteria cells, actinomycetes cells yeast cells, fungi cells, plant cells, animal cells and the like. Concretely, generally, enterobacteria such as *Escherichia coli*, preferably *Escherichia coli*, are used as the host cells, because there is a rich store of knowledge about the technology of mass production of proteins by using enterobacteria such as *Escherichia coli*. Hereinafter, one mode of the method of producing a peptide-forming enzyme by using transformed *Escherichia coli* will be described.

As the promoter that expresses a DNA that encodes a peptide-forming enzyme, a promoter that is usually used in the production of heterogeneous protein in *Escherichia coli* can be used. Examples of such a promoter include potent promoters such as a T7 promoter, a lac promoter, a trp promoter, a trc promoter, a tac promoter, and a $P_R$ promoter and $P_L$ promoter of a lambda phage.

To produce the peptide-forming enzyme as an inclusion body of fused protein, a gene that encodes another protein, preferably a peptide that is hydrophilic is ligated to upstream or downstream of the peptide-forming enzyme gene to form a fused protein gene. The gene that encodes such other protein may be any gene that increases an accumulation amount of the fused protein and enhances the solubility of the fused protein after modification and reconstitution step. Candidates therefore include, for example, a T7 gene 10, a β-galactosidase gene, a dehydrofolic acid reductase gene, an interferon-γ gene, an interleukin-2 gene, and a prochymosin gene.

When these genes are ligated to the genes that encode peptide-forming enzymes, the genes are ligated so that reading frames of codons are consistent. For this purpose, it is recommended that the genes be ligated at a proper restriction enzyme site or a synthetic DNA having a proper sequence be utilized.

Further, to increase a production amount of the peptide-forming enzyme, it is preferable in some cases that a terminator, which is a transcription terminating sequence, be ligated to downstream of the fusion protein gene. The terminator includes, for example, a T7 terminator, an fd phage terminator, a T4 terminator, a tetracycline resistant gene terminator, and an *Escherichia coli* trpA gene germinator. As the vectors for introducing a gene that encodes a peptide-forming enzyme or a fused protein between the peptide-forming enzyme and another protein in *Escherichia coli* are preferred so-called multi-copy type vectors, examples of which include a plasmid having a replicator derived from ColE1, for example, a pUC-based plasmid, and a pBR322-based plasmid or derivatives thereof. The "derivatives" as used herein refer to those plasmids that are subjected modification by substitution, deletion, insertion, addition of bases. Note that the modification as used herein includes modifications by a mutation treatment with a mutagen or UV irradiation, or modifications by spontaneous mutation. More specifically, pUC 19, pUC18, pBR322, pHSG299, pHSG298, pHSG399, pHSG398, RSF1010, pMW119, pMW118, pMW219, pMW218 and so forth can be used as the vectors. Besides, vectors such as phage DNAs and transposon DNA can also be used.

To screen transformants, it is preferable that the vectors have markers such as an ampicillin resistant gene. As such plasmids are commercially available expression vectors having potent promoters (a pUC-based vector (manufactured by Takara Shuzo, Co., Ltd.), pRROK-based vector (manufactured by Clonetech Laboratories, Inc.), pKK233-2 (manufactured by Clonetech Laboratories, Inc.) and so forth.

A recombinant DNA is obtained by ligating a DNA fragment in which a promoter, a gene encoding a peptide-forming enzyme or a fused protein between the peptide-forming enzyme and another protein, and a terminator in order and a vector DNA to each other.

By using the recombinant DNA, *Escherichia coli* is transformed. When the *Escherichia coli* is cultured, a peptide-forming enzyme or a fused protein between the peptide-forming enzyme and another protein is expressed and produced. As the host to be transformed, a strain that is usually used in expressing a heterogeneous gene may be used. For example, *Escherichia coli* JM109 strain is preferable. The method for performing transformation and the method of screening transformants are described in, for example, Molecular Cloning, 2nd edition, Cold Spring Harbor Press (1989).

When the peptide-forming enzyme is expressed as a fused protein, it is also possible to use a restriction protease that recognizes a sequence not existent in the peptide-forming enzyme as a recognition sequence, such as a blood coagulation factor Xa or kallikrein, so that the peptide-forming enzyme can be cut out of the fused protein.

As the production media may be used those media that are usually used for culturing *Escherichia coli*, such as M9-casamino acid medium and LB medium. Further, the culture conditions and production inducing conditions may be properly selected depending on the kinds of marker and promoter of promoter and of host microbe.

To recover the peptide-forming enzyme or the fused protein between the peptide-forming enzyme and another protein, for example, the following methods can be used. If the peptide-forming enzyme or the fused protein thereof is solubilized in the microbial cells, the microbial cells are recovered and then crushed or lyzed and the resultant is used as a crude enzyme solution. Further, the peptide-forming enzyme or fused protein thereof may be used after purifying it by ordinary precipitation, filtration, column chromatography or the like technique, as necessary. In this case, a purification method that uses an antibody to the peptide-forming enzyme or fused protein thereof may be utilized.

When inclusion bodies of protein are formed, the inclusion bodies of protein are solubilized with the modifier. The peptide-forming enzyme may be solubilized together with microbial cell proteins. However, taking subsequent purification operations into consideration, it is preferable that the inclusion bodies be taken out of the microbial cells and then solubilized. To recover the inclusion bodies from the microbial cells, it is sufficient to perform this by a conventionally known method. For example, microbial cells are crushed and inclusion bodies are recovered by centrifugation or the like operation. The modifier for solubilizing the inclusion bodies of protein includes, for example, guanidine hydrochloride (for example, 6M, pH 5 to 8) or urea (for example, 8 M).

By removing the modifier for the solubilized solution by the operations such as dialysis, the protein is recovered as mature form. The solution for dialysis includes, for example, Tris-HCl buffer and phosphate buffer in concentrations of 20 mM to 0.5 M at a pH of 5 to 8.

Concentration of the protein at the reconstitution step is preferably retained at about 500 μm/ml or less. To inhibit the reconstituted peptide-forming enzyme from undergoing self crosslinking, it is preferable that dialysis temperature be 5° C. or less. The method of removing the modifier includes besides the dialysis method, a dilution method, an ultrafiltration method, and so forth. Regeneration of activity can be expected by using any one of these methods.

Note that the genetic engineering techniques may be practiced based on the techniques described in literature, such as, for example, Molecular Cloning, 2nd edition, Cold Spring Harbor Press (1989).

Hereinafter, the present invention will be described in more detail using examples. However, the present invention should not be considered to be limited to the example. In this example, quantitative determination of L-alanine, L-alanyl-L-glutamine was performed by a method in which a high performance liquid chromatography is used (column: Insert-siL ODS-2 manufactured by GL Science, Inc.; eluant: aqueous phosphoric acid solution (pH 2.2, 5.0 mM sodium 1-octanesulfonate/methanol=100/15, flow rate: 1.0 ml/min, detection: 210 nm)).

EXAMPLE

Microbes that Produce L-alanyl-L-Glutamine

For culturing bacteria and actinomycetes, use was made of 50 ml aliquots of a medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract, and 10 g of peptone per liter, dispensed each in a 500-ml Sakaguchi flask and sterilized at 115° C. for 15 minutes. To these media were respectively inoculated one loopful of bacteria shown in Table 1(a) and actinomycetes shown in Table 1(b) that were cultured at 30° C. for 24 hours on slant agar media (20 g/l of agar, pH 7.0) containing 5 g of glucose, 10 g of yeast extract, 10 g of peptone, and 5 g of NaCl, and shaking culture of the media was performed at 30° C. at 120 strokes/minute for 17 hours. After completion of the culture, the microbial cells were centrifuged and suspended in a 0.1 M borate buffer (pH 9.0) containing 10 mM EDTA so as to make 100 g/l of wet microbial cells. For culturing yeasts, 50 ml aliquots of a medium (pH 6.0) containing 5 g of glucose, 5 g of ammonium sulfate, 1 g of monopotassium phosphate, 3 g of dipotassium phosphate, 0.5 g of magnesium sulfate, 5 g of yeast extract, 5 g of malt extract, and 10 g of peptone per liter, dispensed each in a 500-ml Sakaguchi flask and sterilized at 115° C. for 15 minutes, were used. To these media were respectively inoculated one loopful of yeasts shown in Table 1(a) below that were cultured at 30° C. for 24 hours on slant agar media (20 g/l of agar, pH 6.0) containing 5 g of glucose, 5 g of yeast extract, 5 g of malt extract, 10 g of peptone, and 5 g of NaCl and shaking culture of the media was performed at 25° C. at 120 strokes/minute for 17 hours. After completion of the culture, microbial cells were centrifuged from these culture media and suspended each in a 0.1 M borate buffer (pH 9.0) containing 10 mM EDTA so as to make 100 g/l of wet microbial cells. For culturing acetic acid bacteria, 50 ml aliquots of a medium (pH 7.0) containing 5 g of glucose, 5 g of ammonium sulfate, 1 g of monopotassium phosphate, 3 g of dipotassium phosphate, 0.5 g of magnesium sulfate (separately sterilized), 5 g of yeast extract, and 5 g of peptone per liter, dispensed each in a 500-ml Sakaguchi flask and sterilized at 120° C. for 20 minutes, were used. To these media were respectively inoculated one loopful of microbes shown in Table 1(c) below that were cultured at 30° C. for 24 hours on slant agar media (20 g/l of agar, pH 7.0) containing 5 g of glucose, 10 g of yeast extract, and 10 g of peptone, and shaking culture of the media was performed at 30° C. at 120 strokes/minute for 24 hours. 1 ml each of the culture media was added to the above-mentioned medium (50 ml/500-ml Sakaguchi flask) and cultured at 30 C for 24 hours. After completion of the culture, microbial cells were centrifuged and suspended each in a 0.1 M borate buffer (pH 9.0) containing 10 mM EDTA so as to make 100 g/l of wet microbial cells. To 0.1 ml each of these microbial cell suspensions was added 0.1 ml of 100-mM borate buffer (pH 9.0) containing 10 mM EDTA, 200 mM L-alanine methyl ester hydrochloride and 400 mM L-glutamine to make a total volume to 0.2 ml, followed by carrying out a reaction at 25° C. for 2 hours. Production amounts (mM) of L-alanyl-L-glutamine (Ala-Gln) on this occasion are shown in Tables 1(a), 1(b), and 1(c).

TABLE 1 (a)

| Microbe | Ala-Gln (mM) |
| --- | --- |
| Achromobacter delmarvae FERM BP-6988 | 4.2 |
| Acinetobacter johnsonii ATCC 9036 | 3.8 |
| Aeromonas salmonicida ATCC 14174 | 1.8 |
| Agrobacterium tumefaciens IFO 3058 | 8.2 |
| Alcaligenes faecalis ATCC 8750 | 6.3 |
| Arthrobacter citreus ATCC 11624 | 2.7 |
| Beijerinckia indica ATCC 9037 | 13.0 |
| Brevibacterium roseum ATCC 13825 | 2.6 |
| Clavibacter michiganense ATCC 7429 | 1.9 |
| Chryseobacterium meningosepticum ATCC 13253 | 3.2 |
| Escherichia coli ATCC 13071 | 1.0 |
| Enterobacter aerogenes ATCC 13048 | 0.8 |
| Erwinia amylovora IFO 12687 | 0.9 |
| Flavobacterium resinovorum ATCC 12524 | 3.8 |
| Kluyvera citrophila FERM BP-6564 | 3.1 |
| Microbacterium imperiale ATCC 8365 | 4.3 |
| Micrococcus luteus ATCC 11880 | 0.9 |
| Mycoplana bullata ATCC 4278 | 7.1 |
| Pantoea ananatis ATCC 23822 | 0.7 |
| Propionibacterium shermanii FERM BP-8100 | 2.9 |
| Listonella anguillarum ATCC 19264 | 2.9 |
| Rhizobium radiobacter ATCC 4720 | 10.2 |
| Rhodococcus rhodochrous ATCC 21198 | 7.0 |
| Salmonella typhimurium FERM BP-6566 | 1.6 |
| Sarcina lutea FERM BP-6562 | 1.9 |
| Serratia grimesii | 0.8 |

TABLE 1 (a)-continued

| Microbe | Ala-Gln (mM) |
|---|---|
| ATCC 14460 | |
| Stenotrophomonas maltophilia ATCC13270 | 1.2 |
| Staphylococcus aureus ATCC 12600 | 0.7 |
| Streptomyces lavendulae ATCC 11924 | 5.1 |
| Vibrio tyrogenes FERM BP-5848 | 30.0 |
| Xanthomonas maltophilia FERM BP-5568 | 9.8 |
| Bullera alba FERM BP-8099 | 1.8 |
| Candida krusei IFO 0011 | 1.3 |
| Cryptococcus terreus IFO 0727 | 2.9 |
| Filobacidium capsuligenum IFO 1119 | 0.6 |
| Geotrichum amycelium ATCC 56046 | 10.6 |
| Pachysolen tannophilus IFO 1007 | 1.9 |
| Rhodosporidium diobovatum IFO 1829 | 4.8 |
| Rhodotorula minuta IFO 0879 | 3.9 |
| Saccharomyces unisporus IFO 0724 | 4.6 |
| Sporoboromyces salmonicolor IFO 1038 | 5.2 |
| Tremella foliacea IFO 9297 | 1.9 |
| Torulaspora delbrueckii IFO 1083 | 1.8 |
| Torulopsis ingeniosa FERM BP-8098 | 2.1 |

TABLE 1 (b)

| Microbe | Ala-Gln (mM) |
|---|---|
| Actinomadura madurae ATCC 19425 | 1.05 |
| Katasatosporia griseola IFO 14371 | 2.32 |
| Micromonospora chersina ATCC 53710 | 0.82 |
| Nocardia globerula ATCC 21602 | 1.02 |
| Oerskovia turbata FERM BP-8122 | 3.02 |
| Saccharothrix australiensis IFO 14444 | 0.34 |
| Streptoverticillium mobaraensis IFO 13819 | 0.14 |

TABLE 1 (c)

| Microbe | Ala-Gln (mM) |
|---|---|
| Gluconobacter oxydans ATCC621 | 10.50 |
| Gluconobacter oxydans IFO3171 | 14.40 |

TABLE 1 (c)-continued

| Microbe | Ala-Gln (mM) |
|---|---|
| Gluconacetobacter hansenii JCM7643 | 0.80 |
| Gluconacetobacter liquefaciens IFO12388 | 20.30 |
| Acetobacter orleanensis IFO3223 | 0.10 |
| Acetobacter pasteurianus ATCC9325 | 18.80 |
| Asaia ethanolifaciens FERM BP-6751 | 13.10 |
| Zucharibacter floricola FERM BP-6752 | 0.20 |

INDUSTRIAL APPLICABILITY

According to the present invention, a dipeptide can be produced from an amino acid ester and an amino acid that are available at low costs, so that production costs for dipeptides that are useful as materials for pharmaceuticals and functional foods can be reduced. Moreover, various types of dipeptides can be produced from various kinds of amino acid esters and amino acids as raw materials.

The invention claimed is:

1. A method for producing alanyl-glutamine, comprising:
producing alanyl-glutamine by reacting an alanine ester and glutamine using a member selected from the group consisting of: a culture of a microbe, microbial cells separated from the culture, a treated microbial cell product, and a peptide-forming enzyme derived from the microbe;
wherein:
the microbe belongs to a genus selected from the group consisting of Achromobacter, Acinetobacter, Aeromonas, Agrobacterium, Alcaligenes, Arthrobacter, Beijerinckia, Brevibacterium, Clavibacter, Cryseobacterium, Escherichia, Enterobacter, Erwinia, Flavobacterium, Kluyvera, Microbacterium, Micrococcus, Mycoplana, Pantoea, Propionibacterium, Listonella, Rhizobium, Rhodococcus, Salmonella, Sarcina, Serratia, Stenotrophomonas, Staphylococcus, Streptomyces, Vibrio, Xanthomonas, Bullera, Candida, Cryptococcus, Filobacidium, Geotrichum, Pachysolen, Rhodosporidium, Rhodotorula, Sporoboromyces, Tremella, Torulaspora, Torulopsis, Acetobacter, Gluconobacter, Gluconacetobacter, Asaia, Zucharibacter, Actinomadura, Kitasatosporia, Micromonospora, Nocardia, Oerskovia, Saccharothrix, Saccharomyces, and Streptoverticillium;
the microbe has an ability to produce alanyl-glutamine from the alanine ester and glutamine;
the reaction of the alanine ester and glutamine proceeds by the following formula:

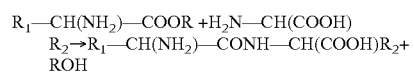

wherein R represents a substituted or unsubstituted hydrocarbon chain, $R_1$ represents a $CH_3$, and $R_2$ represents $(CH_2)_2CONH_2$.

2. The method according to claim 1, wherein producing alanyl-glutamine by reacting the alanine ester and glutamine comprises adding a metal enzyme inhibitor to a reaction mixture of the alanine ester and glutamine.

3. The method according to claim 1, wherein the alanine ester is an L-alanine ester.

4. The method according to claim 1, wherein the glutamine is L-glutamine.

5. The method according to claim 2, wherein the alanine ester is an L-alanine ester.

6. The method according to claim 2, wherein the glutamine is L-glutamine.

7. The method according to claim 3, wherein the glutamine is L-glutamine.

* * * * *